(12) United States Patent
Serafini et al.

(10) Patent No.: US 6,582,936 B1
(45) Date of Patent: *Jun. 24, 2003

(54) METHODS FOR MAKING NUCLEIC ACIDS

(75) Inventors: Tito Serafini, San Francisco, CA (US); Percy Luu, Oakland, CA (US); John Ngai, Berkeley, CA (US); David Lin, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,570

(22) Filed: May 8, 2000

Related U.S. Application Data

(63) Continuation-in-part of application No. 09/049,806, filed on Mar. 27, 1998, now Pat. No. 6,114,152.
(60) Provisional application No. 60/069,589, filed on Dec. 12, 1997.

(51) Int. Cl.[7] ............................. C12P 19/34; C12Q 1/68
(52) U.S. Cl. ........................ 435/91.2; 435/6; 435/91.1; 435/91.3; 435/91.5; 536/23.1; 536/24.1; 536/24.3
(58) Field of Search ................................ 435/91.2, 91.3, 435/91.1, 91.5, 91.51, 91.52; 536/23.1, 24.3, 24.1

(56) References Cited

U.S. PATENT DOCUMENTS

| | | | |
|---|---|---|---|
| 4,952,496 A | | 8/1990 | Studier et al. |
| 5,514,545 A | | 5/1996 | Eberwine |
| 5,554,517 A | * | 9/1996 | Davey et al. |
| 5,741,637 A | * | 4/1998 | Rueger et al. |
| 5,753,433 A | * | 5/1998 | Kessler et al. |

FOREIGN PATENT DOCUMENTS

| | | |
|---|---|---|
| JP | H5-500012 | 1/1993 |
| WO | 91/18115 | 11/1991 |
| WO | 96/36733 | 11/1996 |

OTHER PUBLICATIONS

R Tellier et al., Proc.Natl.Acad.Sci. USA, "Amplification of the full–length hepatitis A virus genome by long reverse transcription–PCR and transcription of infectious RNA directly from the amplicon," Apr. 1996, vol. 93, pp. 4370–4373.*

Ronald R. Breaker, Continuous in Vitro Evolution of Bacteriophage RNA Polymerase Promoters, Biochemistry, 1994, 33 pp. 11980–11986.*

Bertrand et al. PNAS, USA, 1993 90:3496–500.

Gething et al. Nature, 1980 287:301–306.

Toellner KM et al. : "The use of reverse transcription polymerase chain reaction to analyse large numbers of mRNA species from a single cell" Journal of Immunological Methods, vol. 191, 1996, pp. 71–75.

Liu et al., NAR, 21 (21): 4954–4960.

Brady et al., Methods in Mol. & Cell. Biol., 2: 17–25.

* cited by examiner

*Primary Examiner*—John L. LeGuyader
*Assistant Examiner*—M Schmidt
(74) *Attorney, Agent, or Firm*—Richard Aron Osman

(57) ABSTRACT

Nucleic acids are made by converting a primed single-stranded DNA to a double-stranded DNA by a method comprising the step contacting the single-stranded DNA with a DNA polymerase having 5' exonuclease activity under conditions whereby the DNA polymerase converts the-single stranded DNA to the double-stranded DNA, wherein the single-stranded DNA is primed with oligonucleotide primer comprising a sequence complementary to the 3' end of the single-stranded DNA, and at least one of the 5' end of the primer and the single-stranded DNA comprises an RNA polymerase promoter joined to an upstream (5') flanking moiety which protects the promoter from the 5' exonuclease activity of the DNA polymerase.

28 Claims, 2 Drawing Sheets

METHODS FOR MAKING NUCLEIC ACIDS

CROSS REFERENCE TO RELATED APPLICATION

This application is a Continuation-in-Part of application Ser. No. 09/049,806, filed Mar. 27, 1998, now U.S. Pat. No. 6,114,152, and entitled Methods for Making Nucleic Acids, which claims priority to U.S. Provisional Application No. 60/069,589, Dec. 12, 1997, entitled Methods for Making Nucleic Acids, all by Tito Serafini, Percy Luu, John Ngai and David Lin.

The disclosed inventions were made with Government support under Grant (Contract) Nos. GM07048, 1RO1DC02253 and 5F32DC00193-03 awarded by the National Institutes of Health. The government may have rights in these inventions.

INTRODUCTION

1. Field of the Invention

The field of this invention is making nucleic acids.

2. Background

The ability to characterize cells by gene expression provides a wide variety of applications in therapy, diagnostics and bio/medical technology. However, in many of these application, the starting or source material such as stem cells, cancerous cells, identified neurons, embryonic cells, etc. is highly limiting, making it necessary to amplify the targeted mRNA populations. Two existing methods for amplifying mRNA populations suffer from significant limitations. One method, the Brady and Iscove method (Brady et al., 1990, Methods Mol & Cell Biol 2, 17–25), produces only short (200–300 bp), extreme 3' fragments of mRNAs using a PCR-based method which exponentially amplifies artifacts. A second method, the Eberwine protocol (Eberwine et al. (1992) Proc.Natl.Acad.Sci USA 89, 3010–3014) provides sequential linear amplification steps and is the current method of choice for amplifying mRNA populations from limiting material. Nevertheless, this protocol suffers from a number of deficiencies. For example, the amplified product does not represent full-length aRNA for many endogenous mRNAs, and hence the method is of limited use for generating probes or cDNA libraries.

Relevant Literature

Sippel (1973) Eur.J.Biochem. 37, 31–40 discloses the characterization of an ATP:RNA adenyltransferase from *E. coli* and Wittmann et al. (1997) Biochim.Biophys.Acta 1350, 293–305 disclose the characterization of a mammalian poly(A) polymerase. Gething et al. (1980) Nature 287, 301–306 disclose the use of an ATP:RNA adenyltransferase to polyadenylate the '3 termini of total influenza virus RNA. Eberwine et al. (1996) U.S. Pat. No. 5,514,545 describes a method for characterizing single cells based on RNA amplification. Eberwine et al. (1992) Proc.Natl.Acad.Sci USA 89, 3010–3014, describe the analysis of gene expression in single live neurons. Gubler U and Hoffman B J. (1983) Gene (2–3), 263–9, describe a method for generating cDNA libraries, see also the more recent reviews, Gubler (1987) Methods in Enzymology, 152, 325–329 and Gubler (1987) Methods in Enzymology, 152, 330–335. Clontech (Palo Alto, Calif.) produces a "Capfinder" cloning kit that uses "GGG" primers against nascent cDNAs capped with by reverse transcriptase, Clontechniques 11, 2–3 (October 1996), see also Maleszka et al. (1997) Gene 202, 39–43.

SUMMARY OF THE INVENTION

The invention provides methods and compositions for making nucleic acids. The general methods comprise the steps of adding a known nucleotide sequence to the 3' end of a first RNA having a known sequence at the 5' end to form a second RNA and reverse transcribing the second RNA to form a cDNA. According to one embodiment, the first RNA is an amplified mRNA, the known sequence at the 5' end comprises a poly(T) sequence, the adding step comprises using a polyadenyltransferase to add a poly(A) sequence to the 3' end, and the reverse transcribing step is initiated at a duplex region comprising the poly(T) sequence hybridized to the poly(A) sequence. The resultant cDNA transcript may be single-stranded, isolated from the second RNA and optionally converted to double-stranded cDNA, preferably by a DNA polymerase initiating at a noncovalently joined duplex region. The cDNA may also be transcribed to form one or more third RNAs. In another embodiment, the first RNA is made by amplifying a mRNA by the steps of hybridizing to the poly(A) tail of the mRNA a poly(T) oligonucleotide joined to an RNA polymerase promoter sequence, reverse transcribing the mRNA to form single-stranded cDNA, converting the single-stranded cDNA to a double-stranded cDNA and transcribing the double-stranded cDNA to form the first RNA.

In a particular aspect, nucleic acids are made by converting a primed single-stranded DNA to a double-stranded DNA by a method comprising the step contacting the single-stranded DNA with a DNA polymerase having 5' exonuclease activity under conditions whereby the DNA polymerase converts the-single stranded DNA to the double-stranded DNA, wherein the single-stranded DNA is primed with oligonucleotide primer comprising a sequence complementary to the 3' end of the single-stranded DNA, and at least one of the 5' end of the primer and the single-stranded DNA comprises an RNA polymerase promoter joined to an upstream (5') flanking moiety which protects the promoter from the 5' exonuclease activity of the DNA polymerase.

DETAILED DESCRIPTION OF PREFERRED EMBODIMENTS OF THE INVENTION

The following preferred embodiments and examples are offered by way of illustration and not by way of limitation.

Figure 2:
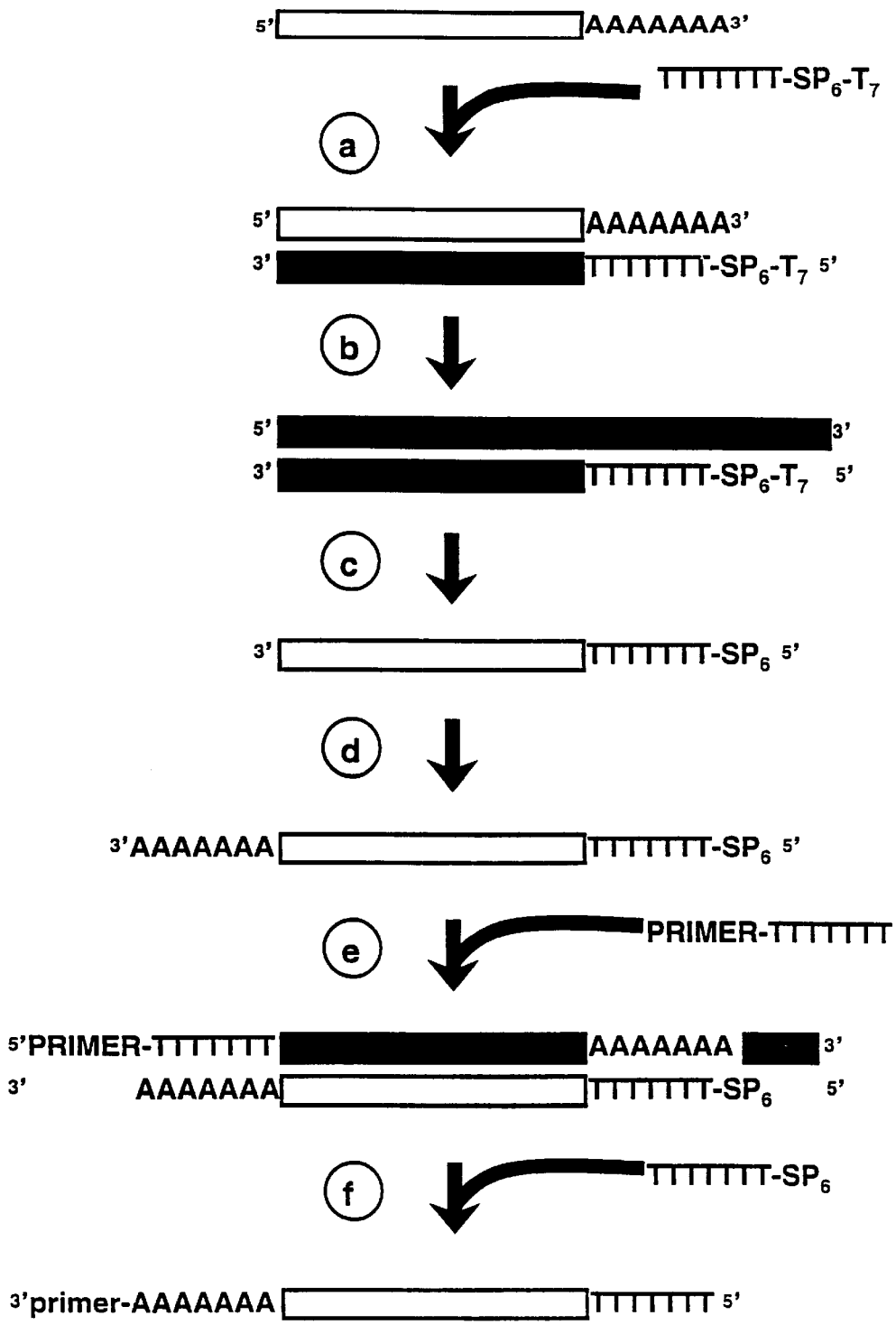
FIG. 2 is a schematic of another embodiment of the invention using a second promoter sequence.

The general methods comprise the steps of adding a known nucleotide sequence to the 3' end of a first RNA having a known sequence at the 5' end to form a second RNA and reverse transcribing the second RNA to form a cDNA. The known sequence at the 5' end of the first RNA species is sufficient to provide a target for a primer and otherwise determined largely by the nature of the starting material. For example, where the starting material is mRNA, the known sequence at the 5' end may comprise a poly(A) sequence and/or (b) an internal mRNA sequence of an mRNA. Alternatively, where the starting material is amplified RNA, or aRNA, the known sequence may comprise a poly(T) sequence or the complement of a known internal mRNA sequence. The known 5' sequence may advantageously comprise additional sequences such as primer target sites, RNA polymerase sites, etc. For example, the presence of both a primer target site such as a poly(T) sequence and an RNA polymerase promoter sequence permits enhanced opportunities for downstream amplification or transcription (see FIG. 2 and related text below).

The adding step may be effect by any convenient method. For example, a polyadenyltransferase or poly(A) polymerase may be used to add selected nucleotides to the 3' end. Poly(A) polymerases may be derived from a wide variety of prokaryotic and eukaryotic sources, are commercially available and well-characterized. In another example, a ligase may be used to add one or more selected oligonucleotides. These enzymes are similarly readily and widely available from a wide variety of sources and are well characterized.

The added known 3' sequence is similarly sufficient to provide a target for a primer, otherwise the nature of the added known sequence is a matter of convenience, limited only by the addition method. For example, using ligase mediated oligonucleotide addition, essentially any known sequence that can be used as target for a primer may be added to the 3' end. With polyadenyltransferase mediated addition, it is generally more convenient to add a poly(N) sequence, with many such transferases demonstrating optimal efficiency when adding poly(A) sequence. Fore polyadenyltransferase mediated additions, the added sequence will generally be in the range of 5 to 50 nucleotides, preferably in the range of 6 to 25 nucleotides, more preferably in the range of 7 to 15 nucleotides.

The reverse transcribing step is initiated at a noncovalently joined duplex region at or near the '3 end of the second RNA species (the first species with the added 3' sequence), generally formed by adding a primer having sufficient complementarity to the 3' end sequence to hybridize thereto. Hence, where the 3' end comprises a poly(A) sequence, the reverse transcribing step is preferably initiated at a duplex region comprising a poly(T) sequence hybridized to the poly(A) sequence. For many applications, the primer comprises additional functional sequence such as one or more RNA polymerase promoter sequences such as a T7 or T3 RNA polymerase promoter, one or more primer sequences, etc.

In a preferred embodiment, the RNA polymerase promoter sequence is a T7 RNA polymerase promoter sequence comprising at least nucleotides −17 to +6 of a wild-type T7 RNA polymerase promoter sequence, preferably joined to at least 20, preferably at least 30 nucleotides of upstream flanking sequence, particularly upstream T7 RNA polymerase promoter flanking sequence. Additional downstream flanking sequence, particularly downstream T7 RNA polymerase promoter flanking sequence, e.g. nucleotides +7 to +10, may also be advantageously used. For example, in one particular embodiment, the promoter comprises nucleotides −50 to +10 of a natural class III T7 RNA polymerase promoter sequence. Table 1 provides exemplary promoter sequences and their relative transcriptional efficiencies in the subject methods (the recited promoter sequences are joined to a 23 nucleotide natural class III T7 promoter upstream flanking sequence).

Table I. Transcriptional efficiency of T7 RNA polymerase promoter sequences.

TABLE I

Transcriptional efficiency of T7 RNA polymerase promoter sequences.

| Promoter Sequence | Transcriptional Efficiency |
|---|---|
| T AAT ACG ACT CAC TAT AGG GAG A (SEQ ID NO:1, class III T7 RNA polymerase promoter) | ++++ |
| T AAT ACG ACT CAC TAT AGG CGC (SEQ ID NO:2, Eberwine et al. (1992) supra) | + |

TABLE I-continued

Transcriptional efficiency of T7 RNA polymerase promoter sequences.

| Promoter Sequence | Transcriptional Efficiency |
|---|---|
| T AAT ACG ACT CAC TAT AGG GCG A (SEQ ID NO:3, Bluescript, Stratagene, La Jolla, CA) | + |

The transcribed cDNA is initially single-stranded and may be isolated from the second RNA by any of wide variety of established methods. For example, the method may involve treating the RNA with a nuclease such as RNase H, a denaturant such as heat or an alkali, etc., and/or separating the strands electrophoretically. The second strand cDNA synthesis may be effected by a number of well established techniques including 3'-terminal hairpin loop priming or methods wherein the polymerization is initiated at a noncovalently joined duplex region, generated for example, by adding exogenous primer complementary to the 3' end of the first cDNA strand or in the course of the Hoffman-Gubler protocol. In this latter embodiment, the cDNA isolation and conversion to double-stranded cDNA steps may be effected together, e.g. contacting the RNA with an RNase H and contacting the single-stranded cDNA with a DNA polymerase in a single incubation step. In any event, these methods can be used to construct cDNA libraries from very small, e.g. single cell, starting materials.

In a particular embodiment, the methods further comprise the step of repeatedly transcribing the single or double-stranded cDNA to form a plurality of third RNAs, in effect, amplifying the first RNA species. Preferred transcription conditions employ a class III T7 promoter sequence (SEQ ID NO:1) and a T7 RNA polymerase under the following reaction conditions: 40 mM Tris pH 7.9, 6 mM $MgCl_2$, 2 mM Spermidine, 10 mM DTT, 2 mM NTP (Pharmacia), 40 units RNAsin (Promega), 300–1000 units T7 RNA Polymerase (6.16 Prep). The enzyme is stored in 20 mM HEPES pH 7.5, 100 mM NaCl, 1 mM EDTA, 1 mM DTT and 50% Glycerol at a protein concentration of 2.5 mg/mL and an activity of 300–350 units/uL. In exemplary demonstrations, 1–3 uL of this polymerase was used in 50 uL reactions. Starting concentrations of template can vary from picogram quantities (single cell level) to 1 ug or more of linear plasmid DNA. The final NaCl concentration is preferably not higher than 6 mM.

Figure 1:
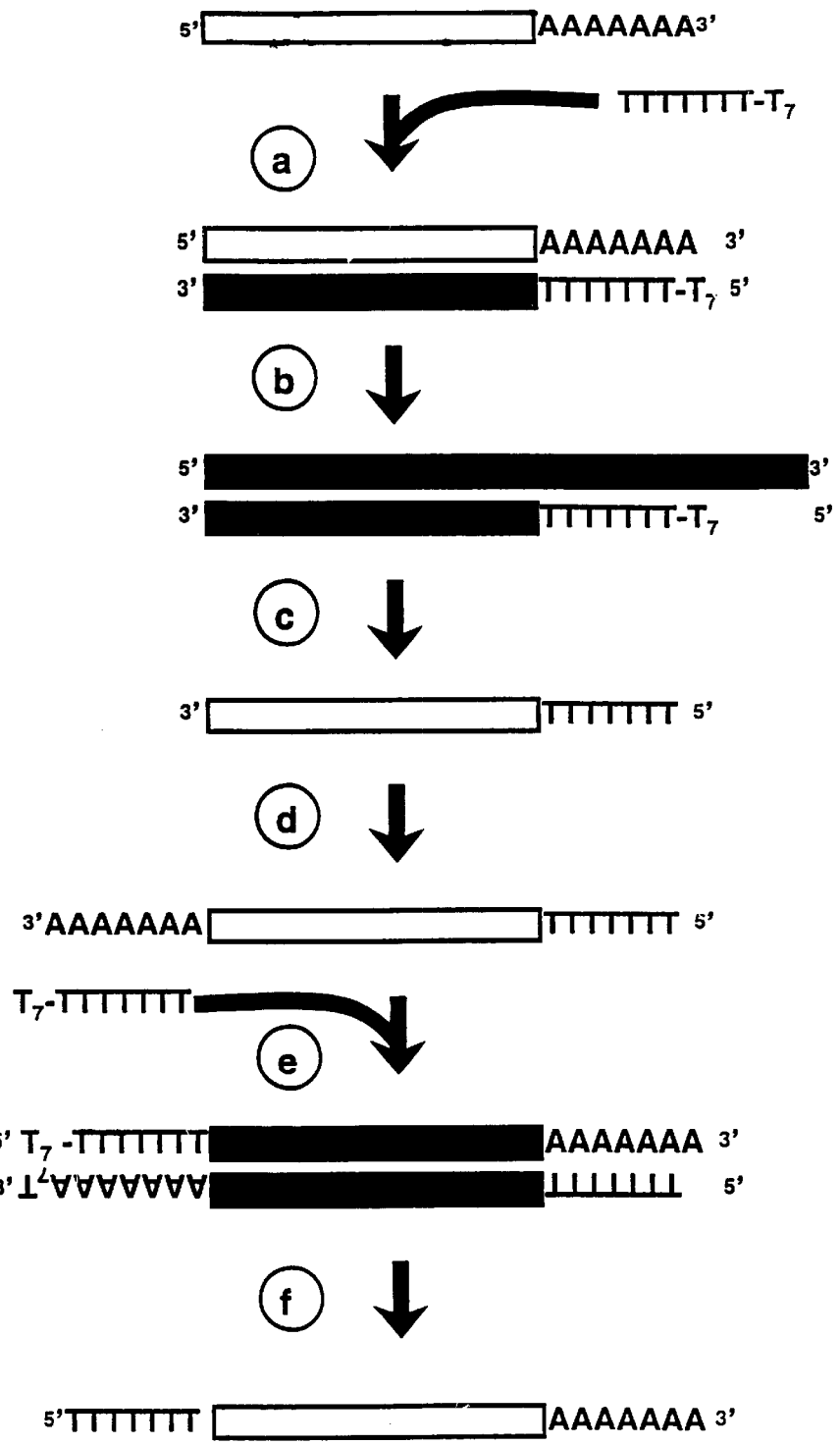
FIG. 1 is a schematic of one embodiment of the invention for amplifying mRNA.

In a more particular embodiment, the first RNA is itself made by amplifying an RNA, preferably a mRNA. For example, the first RNA may be made by amplifying a mRNA by the steps of hybridizing to the poly(A) tail of the mRNA a poly(T) oligonucleotide joined to an RNA polymerase promoter sequence, reverse transcribing the mRNA to form single-stranded cDNA, converting the single-stranded cDNA to a double-stranded cDNA and transcribing the double-stranded cDNA to form the first RNA. FIG. 1 is a schematic of this serial mRNA amplification embodiment of the invention, highlighting individual steps of the method:

(a) An oligonucleotide primer, consisting of 5'-$T_7$-RNA polymerase promoter-oligo $(dT)_{24}$-3', is annealed to the poly(A) tract present at the 3' end of mature mRNAs, and first-strand cDNA is synthesized using reverse transcriptase, yielding an RNA-DNA hybrid (RNA is denoted by open boxes; DNA by filled boxes);

(b) The hybrid is treated with RNase H, DNA polymerase, and DNA ligase to convert the single-stranded cDNA into double-stranded cDNA;

(c) T$_7$ RNA polymerase is used to synthesize large amounts of amplified RNA (aRNA) from this cDNA. The incorporation of a modified T$_7$ polymerase promoter sequence into our primer, as compared to the altered promoter sequence utilized by Eberwine et al., *PNAS* 89: 3010–3014, 1992, greatly increases the yield of aRNA;

(d) The aRNA is tailed with poly(A) using a poly(A) polymerase. This modification generates much longer first-strand cDNA in the next step as compared to the original protocol;

(e) After denaturation and elimination of the aRNA, a T$_7$-RNA polymerase promoter-oligo (dT) primer is annealed to this newly synthesized poly(A) sequence, and reverse transcriptase is used to synthesize first-strand cDNA. Second-strand cDNA and the complementary strand of the polymerase promoter are synthesized as in (b); and (f) T$_7$ RNA polymerase is then used to generate aRNA from this cDNA template.

Another embodiment involves the incorporation of additional sequences during certain synthesis steps. These sequences allow, for example, for the PCR amplification of the amplified RNA, for direct second-round amplification without synthesizing a full second strand cDNA, etc. This embodiment is diagramed in FIG. 2:

(a) This is step (a) of FIG. 1, except that the primer for first strand cDNA synthesis also includes a promoter site for a different RNA polymerase (shown with SP$_6$; T$_3$ RNA polymerase site is also possible) between the poly(T) and the T$_7$ sequences;

(b) This is step (b) of FIG. 1;

(c) This is step (c) of FIG. 1, except that the aRNA now has an RNA polymerase site at its 5' end;

(d) This is step (d) of FIG. 1;

(e) This is step (e) of FIG. 1, except that the oligonucleotide used for priming first strand cDNA synthesis also has an additional sequence at its 5' end suitable for use as a priming site during polymerase chain reaction (PCR). Note also that the SP$_6$ or T$_3$ RNA polymerase site has been copied into first strand cDNA. Because this first strand cDNA has unique sequences at both its 5' and 3' ends, it can now be used directly in a PCR reaction for total amplification of all sequences, as an alternative to performing another round of aRNA synthesis;

(f) The first strand cDNA can be used directly for aRNA synthesis by annealing an oligonucleotide incorporating the complementary portion of the SP$_6$ or preferably, the T$_3$ RNA polymerase site. Or, the first strand cDNA can be converted into double-stranded cDNA through second strand synthesis, with aRNA synthesis then following.

Improved Linear Amplification Protocol

Primer Sequence: (b-dT-T7(6)): 5' biotin-AAAT-T7 promoter (SEQ ID NO:1)-CCACA-(T)$_{21}$ 3'

1. First Round Reactions (a) Reverse Transcription add primer to 10–100×molar excess; e.g., for 100 ng total RNA, use 1 ng b-dT-T7(6) primer for 1 ng total RNA, use 100 pg primer.

11 μl total RNA
1 μl b-dT-TO7(6) primer
heat 70 C., 5 min
chill on ice
add on ice:
4 μl 5×1st strand buffer (250 mM Tris-HCl (pH 8.3), 375 mM KCl, 15 mM MgCl$_2$, New England Biolabs)
2 μl 0.1 M DTT 1 μl 10 mM (each) dNTP stock
1 μsuperscript II (200 U; Gibco-BRL)
incubate room temperature, 10 min; then 42 C., 50 min
chill on ice (For Single-cell Reactions)
10 pg primer
11 μl water containing 0.5% Igepal-630 non-ionic detergent (Sigma)
4 μl 5×1st strand buffer (Gibco-BRL)
collect cell into mixture
heat 70 C., 1 min
chill on ice
add remaining reagents and proceed as described (b) 2nd Strand Synthesis
add to first strand reaction:
57 μl ddH20
20 μl 5×2nd Strand Buffer (100 mM Tris-HCl (pH 6.9), 450 mM KCl, 23 mM MgCl$_2$, 0.75 mM beta-NAD+, 50 mM (NH$_4$)$_2$SO$_4$, Gibco-BRL)
1.5 μl 10 mM (each) dNTP stock
1 μl *E. coli* DNA Polymerase I holoenzyme (10 U/μl; New England Biolabs)
0.5 μl RNAase H (2.2 U/μl; Gibco-BRL)
incubate 16 C., 4 hr
phenol extract and precipitate Microdialysis
resuspend first round cDNA in 15 μl 10 mM 10 mM Tris-HCl (pH 7.4)
wet 0.025 μm pore Millipore nitrocellulose filter on 50 mls of 10 mM Tris-HCl (pH 7.4)
Pipet cDNA onto Filter
dialyze two hours at room temperature
collect dialyzed cDNA; "wash" filter with 10 μl ddH$_2$O to retrieve remaining cDNA.

(c) Transcription Reaction
15 μl cDNA
2.5 μl 10×Transcription buffer (400 mM Tris-HCl (pH 7.9), 60 mM MgCl$_2$, 100 mM NaCl, 20 mM Spermidine)
2.5 μl 0.1 M DTT
2 μl 25 mM (each) NTP stock
0.5 μl RNAsin (Promega)
add T7 RNA polymerase (to 15 U/μl final)
add ddH20 to 25 μl final
incubate 40 C., 4–6 hr (d) Tailing Reaction
add directly to transcription reaction:
3.6 μl 5M NaCl
6 μl 100 mM MgCl2
40.4 μl ddH20
1 unit *E. coli* poly(A) polymerase (Amersham)
incubate 37 C., 15 min
phenol extract and precipitate 2. Second Round Reactions
(e) Reverse Transcription
add 10× more primer than in previous round; e.g., add 10 ng primer to a first round amplification reaction having 100 ng total RNA (f) Repeat Protocols as Before Except Do Not Tail Second Round Reaction Notes: (1) In this protocol, the primer comprises the native 23 nucleotide T7 RNA polymerase promoter sequence (SEQ ID NO:1) and a polyT 3' tail. The 5' end of the promoter is joined to an upstream flanking moiety which serves to protect the critical 23 nucleotide sequence from 5' exonuclease activity, e.g. from DNA Pol I. The moiety may be 5' nucleotides, such as upstream T7 polymerase promoter flanking sequence as described and exemplified above with nucleotides −50 to −16 of the T7 promoter. However, any other protecting moieties can be substituted for the flanking nucleotides, so long as they are compatible with the overall protocol (e.g. do not interfere with any required polymerization reaction) and similarly protect the critical 23 nucleotide sequence; examples include dyes like fluorescein and rhodamine, modified nucleotides like digoxigenin, a sterol, such as cholesterol and derivatives thereof, affinity tags like biotin, etc. These moieties may be used alone, in conjunction with additional protective flanking or linking nucleotides (e.g. the AAAT linker, herein). The 3' end of the promoter and the polyT tail may also be linked directly or through a linker. Preferred linkers, such as the native 3' flanking nucleotides of the T7 promoter as described and exemplified above with nucleotides +7 to +10, enhance polymerization with difficult templates. Other enhancing linkers (e.g. the CCACA linker, herein) may be substituted.

(2) Numerous aspects of the protocol are discretionary, and may provide improved yield or promote efficiency, depending on the application. For example, a wide range of RNA polymerase promoters may be used, including phage (e.g. T3, T7, SP-6) and eukaryotic promoters (e.g. CMV, EF-1α, β-actin, thymidine kinase (TK), herpes PK, PGK and NF-κB-responsive RNA polymerase promoters), etc. Similarly, a wide variety of suitable primers may be fashioned according to the invention (primers may also be generated from hairpin structure of the single-stranded DNA). Further, while a broad range of primer concentrations are effective, we generally find 10–100× molar excess to be optimal; for single cell reactions, we find use of a non-ionic detergent, such as Igepal-630, improves yield; during second strand synthesis, we find ligase may be omitted from the reaction; we find that the amount of DNA polymerase used can often be substantially reduced from published methods which often require 30 U/ul, and lowering the polymerase concentration also reduces the 5' exonuclease activity present in the reaction; we find introducing a microdialysis step prior to the transcription reaction improves yield, as does our use of 2 mM dNTP concentrations, 400 uM ATP concentration, and adding 10× more primer in the second round of amplification.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for making a nucleic acid comprising the step of:
converting a primed single-stranded DNA to a double-stranded DNA by a method comprising the step of contacting the single-stranded DNA with a DNA polymerase having 5' exonuclease activity under conditions whereby the DNA polymerase converts the single-stranded DNA to the double-stranded DNA,
wherein the 5' end of the single-stranded DNA comprises an RNA polymerase promoter joined to an upstream (5') flaking moiety which protects the promoter from the 5' exonuclease activity of the DNA polymerase, wherein the upstream flanking moiety is selected from the group consisting of a dye, nucleotides −50 to −16 of the T7 promoter, modified nucleotide, a sterol, and an affinity tag.

2. A method according to claim 1, wherein the RNA polymerase promoter is selected from the group consisting of a T7, a T3 and an SP-6 RNA polymerase promoter.

3. A method according to claim 1, wherein the RNA polymerase promoter comprises SEQ ID NO:1.

4. A method according to claim 1, wherein the upstream flanking moiety is selected from the group consisting of a dye, a modified nucleotide, a sterol, and an affinity tag.

5. A method according to claim 1, wherein the upstream flanking moiety is selected from the group consisting of fluorescein, rhodamine, digoxigenin, cholesterol and biotin.

6. A method according to claim 1, wherein the upstream flanking moiety is biotin.

7. A method according to claim 1, wherein the RNA polymerase promoter comprises SEQ ID NO:1 and the upstream flanking moiety is nucleotides −50 to −16 of the T7 promoter.

8. A method according to claim 1, further comprising the step of repeatedly transcribing the double stranded DNA.

9. A method according to claim 1, wherein the primed single-stranded DNA is made by the steps of:
reverse transcribing an RNA to form a heterohybrid of the RNA and the single-stranded DNA; and
nicking the RNA with an RNA endonuclease under conditions whereby the single-stranded DNA retains a 5' most fragment of the RNA hybridized at the 3' end of the single-stranded DNA.

10. A method according to claim 9, wherein the RNA is mRNA and the reverse transcribing step comprises hybridizing to a 3' poly(A) tail of the mRNA a poly(T) oligonucleotide joined to the RNA polymerase promoter sequence.

11. A method according to claim 9, wherein the RNA is aRNA made by amplifying an mRNA and the reverse transcribing step comprises adding a known sequence onto the 3' end of the aRNA, hybridizing to the known sequence a complementary oligonucleotide joined to the RNA polymerase promoter sequence.

12. A method according to claim 9, wherein the RNA is aRNA made by amplifying an mRNA and the reverse transcribing step comprises using polyadenyltransferase to add a known sequence onto the 3' end of the aRNA, hybridizing to the known sequence a complementary oligonucleotide joined to the RNA polymerase promoter sequence.

13. A method according to claim 9, wherein the RNA is aRNA made by amplifying an mRNA and the reverse transcribing step comprises using polyadenyltransferase to add a poly(A) tail onto the 3' end of the aRNA, hybridizing to the poly(A) tail sequence a complementary poly(T) oligonucleotide joined to the RNA polymerase promoter sequence.

14. A method according to claim 9, wherein the RNA polymerase promoter is selected from the group consisting of a T7, a T3 and an SP-6 RNA polymerase promoter.

15. A method according to claim 9, wherein the upstream flanking moiety is selected from the group consisting of a dye, modified nucleotide, a sterol, and affinity tag.

16. A method according to claim 9, wherein the upstream flanking moiety is selected from the group consisting of fluorescein, rhodamine, digoxigenin, cholesterol and biotin.

17. A method according to claim 9, wherein the upstream flanking moiety is biotin.

18. A method according to claim 9, wherein the RNA polymerase promoter comprises SEQ ID NO:1.

19. A method according to claim 9, wherein the RNA polymerase promoter comprises SEQ ID NO:1 and the upstream flanking moiety is nucleotides −50 to −16 of the T7 promoter.

20. A method according to claim 9, further comprising the step of repeatedly transcribing the double stranded DNA.

21. A method for making a nucleic acid comprising the step of:
converting a primed single-stranded DNA to a double-stranded DNA by a method comprising the step of contacting the single-stranded DNA with a DNA polymerase having 5' exonuclease activity under conditions whereby the DNA polymerase converts the single-stranded DNA to the double-stranded DNA,
wherein the single-stranded DNA is primed with an oligonucleotide primer comprising a sequence complementary to the 3' end of the single-stranded DNA and the 5' end of the primer comprises an RNA polymerase promoter joined to an upstream (5') flanking moiety which protects the promoter from the 5' exonuclease activity of the DNA polymerase, wherein the upstream flanking moiety is selected from the group consisting of a dye, nucleotides −50 to −16 of the T7 promoter a modified nucleotide, a sterol, and an affinity tag.

22. A method according to claim 21, wherein the RNA polymerase promoter is selected from the group consisting of a T7, a T3 and an SP-6 RNA polymerase promoter.

23. A method according to claim 21, wherein the upstream flanking moiety is selected from the group consisting of a dye, a modified nucleotide, a sterol, and an affinity tag.

24. A method according to claim 21, wherein the upstream flanking moiety is selected from the group consisting of fluorescein, rhodamine, digoxigenin, cholesterol and biotin.

25. A method according to claim 21, wherein the upstream flanking moiety is biotin.

26. A method according to claim 21, wherein the RNA polymerase promoter comprises SEQ ID NO:1.

27. A method according to claim 21, wherein the RNA polymerase promoter comprises SEQ ID NO:1 and the upstream flanking moiety is nucleotides −50 to −16 of the T7 promoter.

28. A method according to claim 21, further comprising the step of repeatedly transcribing the double stranded DNA.

* * * * *

UNITED STATES PATENT AND TRADEMARK OFFICE
CERTIFICATE OF CORRECTION

PATENT NO. : 6,582,936 B1
DATED : June 24, 2003
INVENTOR(S) : Serafini et al.

Page 1 of 1

It is certified that error appears in the above-identified patent and that said Letters Patent is hereby corrected as shown below:

Column 9,
Line 23, "flaking" should be -- flanking --;
Line 27, "modified nucleotide" should be -- a modified nucleotide --.

Column 10,
Line 30, "modified nucleotide" should be -- a modified nucleotide --;
Line 30, "affinity tag" should be -- an affinity tag --.

Signed and Sealed this

Twelfth Day of August, 2003

JAMES E. ROGAN
*Director of the United States Patent and Trademark Office*

```
                          SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 1:

TAATACGACT CACTATAGGG AGA                                                    23

(2) INFORMATION FOR SEQ ID NO: 2:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 2:

TAATACGACT CACTATAGGC GC                                                     22

(2) INFORMATION FOR SEQ ID NO: 3:

(i) SEQUENCE CHARACTERISTICS:
             (A) LENGTH: 23 base pairs
             (B) TYPE: nucleic acid
             (C) STRANDEDNESS: single
```

-continued

```
      (D) TOPOLOGY: linear (ii) MOLECULE TYPE: other nucleic acid (xi) SEQUENCE DESCRIPTION: SEQ ID NO: 3:

TAATACGACT CACTATAGGG CGA                                            23
```